(12) United States Patent
Baril et al.

(10) Patent No.: US 11,690,648 B2
(45) Date of Patent: Jul. 4, 2023

(54) SURGICAL ACCESS DEVICE AND METHOD FOR USING THE SAME

(71) Applicant: Covidien LP, Mansfield, MA (US)

(72) Inventors: Jacob C. Baril, Norwalk, CT (US); Matthew A. Dinino, Newington, CT (US); Saumya Banerjee, Hamden, CT (US); Scott J. Prior, Shelton, CT (US); Brian J. Creston, Madison, CT (US)

(73) Assignee: Covidien LP, Mansfield, MA (US)

( * ) Notice: Subject to any disclaimer, the term of this patent is extended or adjusted under 35 U.S.C. 154(b) by 374 days.

(21) Appl. No.: 16/808,151

(22) Filed: Mar. 3, 2020

(65) Prior Publication Data

US 2021/0275214 A1   Sep. 9, 2021

(51) Int. Cl.
*A61B 17/34* (2006.01)
*A61M 1/00* (2006.01)
*A61B 17/02* (2006.01)

(52) U.S. Cl.
CPC ...... *A61B 17/3423* (2013.01); *A61B 17/0293* (2013.01); *A61M 1/84* (2021.05); *A61B 2218/008* (2013.01)

(58) Field of Classification Search
CPC .................. A61B 17/0293; A61B 17/3423
See application file for complete search history.

(56) References Cited

U.S. PATENT DOCUMENTS

| | | |
|---|---|---|
| 5,578,000 A | 11/1996 | Greff et al. |
| 5,941,873 A | 8/1999 | Korenfeld |
| 6,033,362 A | 3/2000 | Cohn |
| 6,544,210 B1 | 4/2003 | Trudel et al. |
| 7,789,946 B2 | 9/2010 | Schultz et al. |
| 7,901,353 B2 | 3/2011 | Vayser et al. |
| 9,427,288 B1 | 8/2016 | Chenger et al. |
| 10,076,358 B2 | 9/2018 | Zergiebel et al. |
| 2002/0007150 A1* | 1/2002 | Johnson ............ A61F 9/00745 604/294 |
| 2005/0054993 A1 | 3/2005 | Falahee |
| 2006/0247673 A1 | 11/2006 | Voegele et al. |
| 2011/0054260 A1* | 3/2011 | Albrecht ............ A61B 17/0293 600/208 |
| 2012/0089093 A1 | 4/2012 | Trusty |
| 2013/0184536 A1 | 7/2013 | Shibley et al. |

(Continued)

*Primary Examiner* — Susan S Su
*Assistant Examiner* — Ted Yang
(74) *Attorney, Agent, or Firm* — Carter, DeLuca & Farrell LLP

(57) ABSTRACT

A smoke evacuator for use with a surgical access device includes an evacuation ring having an inner peripheral surface defining one or more channels therein disposed in fluid communication with an operating cavity. A connection port is disposed thereon in fluid communication with the channel(s) and adapted to connect to a smoke evacuation system. The evacuation ring includes a profile having an inner flange that forms part of the inner peripheral surface of the evacuation ring and one or more lower flanges, the inner flange is configured to mechanically engage a rim of an access device and the lower flange(s) is adapted to mechanically engage a wound guard, wherein engagement of the inner flange of the evacuation ring atop the access device and engagement of the lower flange(s) with the wound guard secures the access device, the wound guard and the smoke evacuation ring within the operating cavity.

13 Claims, 13 Drawing Sheets

(56) References Cited

U.S. PATENT DOCUMENTS

| | | |
|---|---|---|
| 2014/0221756 A1* | 8/2014 | Kleyman .......... A61B 17/3423 |
| | | 600/208 |
| 2014/0330285 A1 | 11/2014 | Rosenblatt et al. |
| 2016/0158468 A1 | 6/2016 | Tang et al. |
| 2017/0049427 A1 | 2/2017 | Do et al. |
| 2017/0325657 A1 | 11/2017 | Prior |
| 2018/0008250 A1 | 1/2018 | Joseph |
| 2018/0049771 A1 | 2/2018 | Rhemrev-Pieters |

* cited by examiner

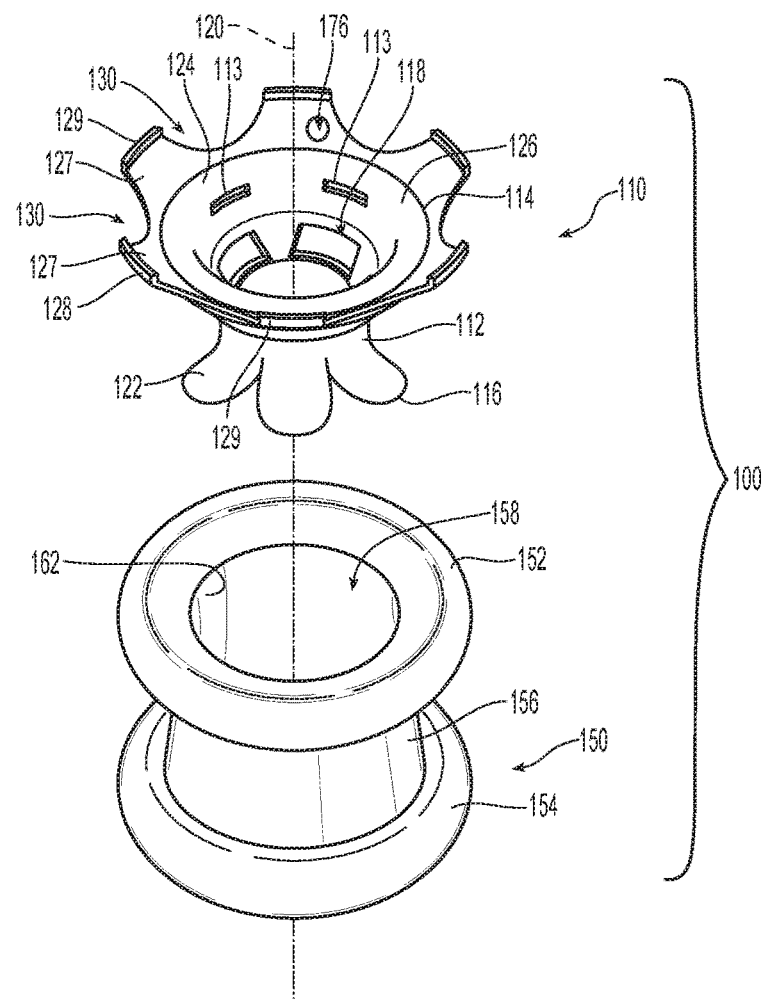
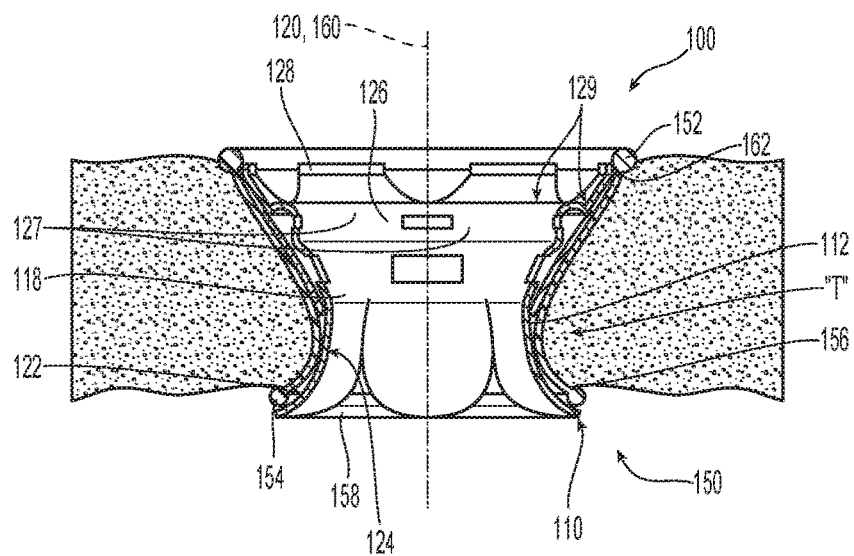
Fig. 1A
Fig. 1B

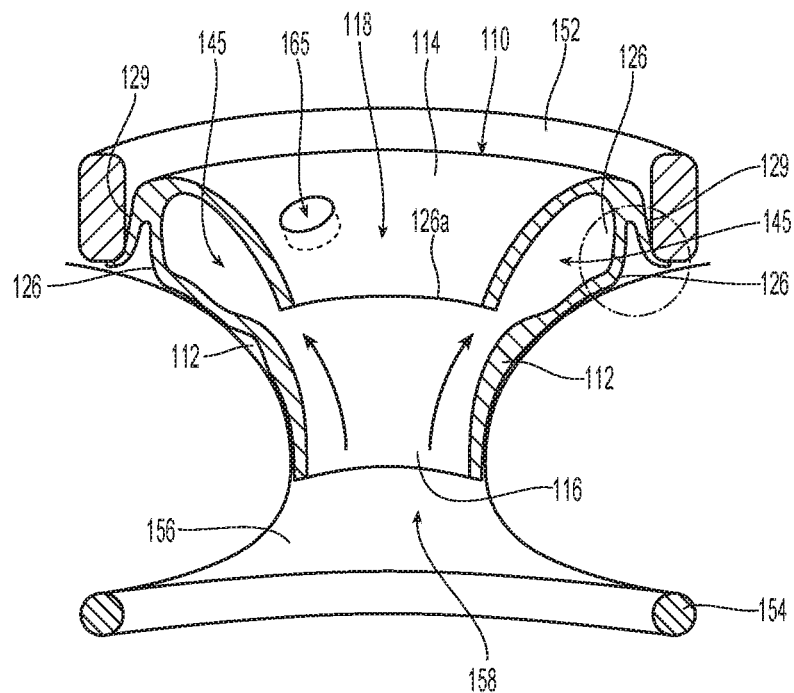
*Fig. 2A*
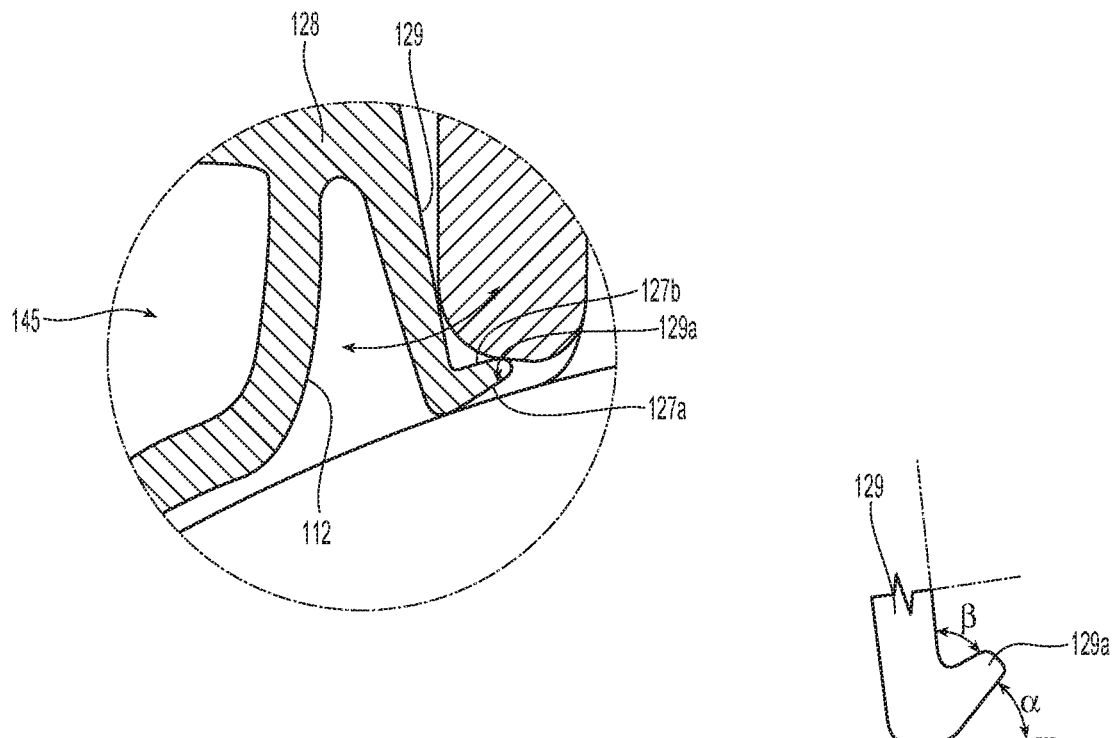
*Fig. 2B*
*Fig. 2C*

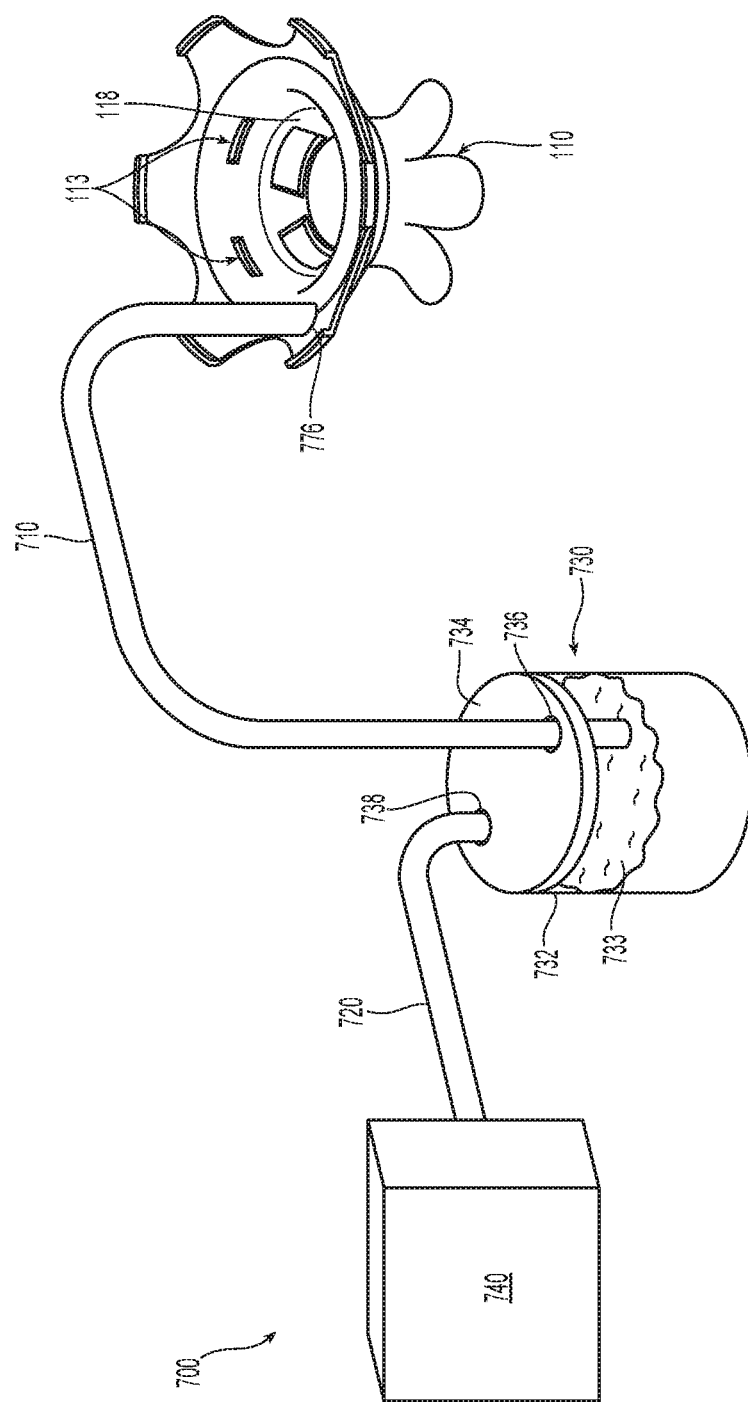

SURGICAL ACCESS DEVICE AND METHOD FOR USING THE SAME

FIELD

The present disclosure relates to tissue specimen removal and, more particularly, to surgical access devices and systems incorporating the same for use in tissue specimen removal procedures and other surgical procedures.

BACKGROUND

In minimally-invasive surgical procedures, operations are carried out within an internal body cavity through small entrance openings in the body. The entrance openings may be natural passageways of the body or may be surgically created, for example, by making a small incision into which a cannula is inserted.

Minimally-invasive surgical procedures may be used for partial or total removal of tissue from an internal body cavity. However, the restricted access provided by minimally-invasive openings (natural passageways and/or surgically created openings) presents challenges with respect to maneuverability and visualization. The restricted access also presents challenges when large tissue specimens are required to be removed. As such, tissue specimens that are deemed too large for intact removal may be broken down into a plurality of smaller pieces to facilitate removal from the internal body cavity. Typically, a surgical sleeve and a specimen containment bag are used for this purpose. Moreover, during specimen rescission, smoke may cloud the operating site and may require evacuation therefrom. Smoke evacuation systems are commonplace for use with the surgical sleeve.

SUMMARY

As used herein, the term "distal" refers to the portion that is described which is further from a user, while the term "proximal" refers to the portion that is being described which is closer to a user. Further, any or all of the aspects described herein, to the extent consistent, may be used in conjunction with any or all of the other aspects described herein.

Provided in accordance with aspects of the present disclosure is a smoke evacuator for use with a surgical access device which includes an evacuation ring having an inner peripheral surface defining one or more channels therein disposed in fluid communication with an operating cavity. A connection port is disposed thereon in fluid communication with the channel(s) and is adapted to connect to a smoke evacuation system. The evacuation ring includes a profile having an inner flange that forms part of the inner peripheral surface of the evacuation ring and one or more lower flanges. The inner flange is configured to mechanically engage a rim of an access device and the lower flange(s) is adapted to mechanically engage a wound guard, wherein engagement of the inner flange of the evacuation ring atop the access device and engagement of the lower flange(s) with the wound guard secures the access device, the wound guard and the smoke evacuation ring within the operating cavity.

In aspects according to the present disclosure, the profile of the evacuation ring is U-shaped and includes an inner flange that forms part of the inner peripheral surface of the evacuation ring, an upper flange and one or more lower flanges, the upper flange is configured to mechanically engage the rim of the access device and the lower flange(s) is adapted to mechanically engage a corresponding number of apertures defined within the wound guard.

In aspects according to the present disclosure, the evacuation ring is resilient to facilitate mechanical engagement atop the access device and with the wound guard. In other aspects according to the present disclosure, the evacuation ring includes an outer peripheral surface configured to complement an adjoining surface of the access device. In still other aspects according to the present disclosure, the profile of the evacuation ring includes a series of lower flanges configured to engage a corresponding series of apertures defined in the wound guard. In yet other aspects according to the present disclosure, the series of lower flanges are arranged in opposing pairs about the evacuation ring.

Provided in accordance with another aspect of the present disclosure is a smoke evacuator for use with a surgical access device which includes an evacuation ring having: an inner peripheral surface having one or more channels defined therein disposed in fluid communication with an operating cavity; a connection port disposed thereon in fluid communication with the channel(s) and adapted to connect to a smoke evacuation system; an elongated sleeve having a ring-like distal end, the ring-like distal end configured to operably engage a distal end of a wound guard to bias the distal end outwardly to engage tissue; and a locking flange disposed at a proximal end thereof adapted to operably engage a proximal ring of an access device, wherein engagement of the locking flange of the evacuation ring with the access device and engagement of the distal end of the elongated sleeve of the evacuation ring with the distal end of the wound guard secures the access device, the wound guard and the smoke evacuation ring within the operating cavity.

In aspects according to the present disclosure, the distal end of the elongated sleeve of the evacuation ring operably engages a pair of bifurcated ends of the wound guard to bias the ends outwardly to engage tissue. In other aspects according to the present disclosure, the locking flange includes one or more locking ends configured to operably engage an underside of the proximal ring of the access device. In yet other aspects according to the present disclosure, the locking flange includes one or more releases configured to uncouple the locking end from the underside of the proximal ring of the access device.

Provided in accordance with another aspect of the present disclosure is a surgical system for accessing a surgical cavity which includes: an access device configured for insertion within an operating cavity; a wound guard configured for insertion within the access device; and a smoke evacuator configured to secure the access device and wound guard within the operating cavity. The smoke evacuator includes an evacuation ring having: an inner peripheral surface having one or more channels defined therein disposed in fluid communication with the operating cavity; a connection port disposed thereon in fluid communication with the channel(s) and adapted to connect to a smoke evacuation system; an elongated sleeve having a ring-like distal end, the ring-like distal end configured to operably engage a distal end of the wound guard to bias the distal end outwardly to engage tissue; and a locking flange disposed at a proximal end thereof adapted to operably engage a proximal ring of the access device, wherein engagement of the locking flange of the evacuation ring with the access device and engagement of the distal end of the elongated sleeve of the evacuation ring with the distal end of the wound guard secures the access device, the wound guard and the smoke evacuation ring within the operating cavity.

In aspects according to the present disclosure, the distal end of the wound guard is bifurcated and the distal end of the elongated sleeve of the evacuation ring operably engages the bifurcated ends of the wound guard to bias the ends outwardly to engage tissue.

In aspects according to the present disclosure, the locking flange includes one or more locking ends configured to operably engage an underside of the proximal ring of the access device. In other aspects according to the present disclosure, the locking flange includes at one or more releases configured to uncouple the locking end from the underside of the proximal ring of the access device.

In aspects according to the present disclosure, the wound guard includes one or more holes defined therein configured to facilitate removal of the wound guard from the access device. In other aspects according to the present disclosure, the bifurcated distal ends of the wound guard are resilient and inwardly biased to facilitate insertion within the access device Provided in accordance with another aspect of the present disclosure is a surgical system for accessing a vaginal cavity which includes an access device configured for insertion within an operating cavity, the access device including an elongated sleeve having a proximal ring disposed at a proximal end thereof and an anchoring ring disposed at a distal end thereof. The anchoring ring is inwardly biased to facilitate insertion within a vaginal canal and the proximal ring is configured to seat against tissue outside the vaginal canal. A wound guard is configured for insertion within the access device. The wound guard includes an elongated sleeve having a proximal ring disposed at a proximal end thereof and biasing ring at a distal end thereof. The biasing ring, upon insertion, is configured to bias the anchoring ring outwardly to engage tissue within the vaginal canal to secure both the access device and wound guard therein.

In aspects according to the present disclosure, the cross sectional profile of the anchoring ring is bulbous to facilitate engagement with tissue within the vaginal canal. In other aspects according to the present disclosure, the proximal ring of the wound guard is configured to seat atop the proximal ring of the access device. In yet other aspects according to the present disclosure, the anchoring ring of the access device is split to include a series of anchoring portions configured in a ring-like manner.

Provided in accordance with another aspect of the present disclosure is a method for sizing a wound guard in a surgical system for accessing a surgical cavity, which includes: inserting an access device within a surgical or natural opening; tenting the access device to secure the access device within the opening; repeatedly inserting one of a series wound guards of varying length within the access port until the wound guard is properly sized therein; and engaging a smoke evacuator atop the access device to secure the wound guard to the access device within the surgical cavity.

In aspects according to the present disclosure, the length of the series of wound guards range from about 2 cm to about 8 cm. In other aspects according to the present disclosure, the smoke evacuator operably engages the wound guard to secure the wound guard to the access device. In yet other aspects according to the present disclosure, the method further includes: attaching a connection port operably associated with the smoke evacuator to a smoke evacuation system; and activating the smoke evacuation system to remove smoke from the operating cavity during surgery Provided in accordance with another aspect of the present disclosure is a surgical system for accessing an operating cavity, which includes an access device configured for insertion within an operating cavity, the access device including an elongated sleeve having proximal and distal rims disposed on opposing sides thereof. The distal rim is configured for insertion within an operating cavity and the proximal rim is configured to seat against tissue outside the operating cavity. A wound guard is configured for insertion within the access device. The wound guard includes a pair of interleaved arcuate portions each having a strap slot defined therein configured to receive a respective strap. Each strap includes a proximal end configured to operably engage the proximal rim of the access device and a distal end configured to engage the distal rim of the access device. In use, tension on the pair of straps during insertion and adjustment of the access device moves the pair of interleaved arcuate portions relative to one another to facilitate properly sizing the wound guard within the access device.

In aspects according to the present disclosure, the pair of interleaved arcuate portions includes a first arcuate portion having a solid distal end and a second arcuate portion having a split distal end defining an elongated slot therein configured to receive the solid distal end. In other aspects according to the present disclosure, adjusting the proximal rim of the access device to secure the access device within the operating cavity automatically adjusts the arcuate portions to size the wound guard therein.

BRIEF DESCRIPTION OF THE DRAWINGS

The above and other aspects and features of the present disclosure will become more apparent in light of the following detailed description when taken in conjunction with the accompanying drawings wherein like reference numerals identify similar or identical elements.

FIG. 1A is an exploded, top, perspective view of a system provided in accordance with the present disclosure including an access device and a tissue guard;

FIG. 1B is a cross-sectional view of the system of FIG. 1A disposed within an opening in tissue;

FIG. 2A is a front cross sectional view of the access device with the tissue guard inserted therein;

FIG. 2B is an enlarged view of the area of detail of FIG. 2A;

FIG. 2C is a greatly-enlarged view showing the engagement of a proximal flange of the tissue guard within a proximal rim the access device;

FIG. 12 is a schematic illustration of a smoke evacuation system for use with one or more of the access devices and wound guards of FIGS. 1A-11.

DETAILED DESCRIPTION

Figure 3A:
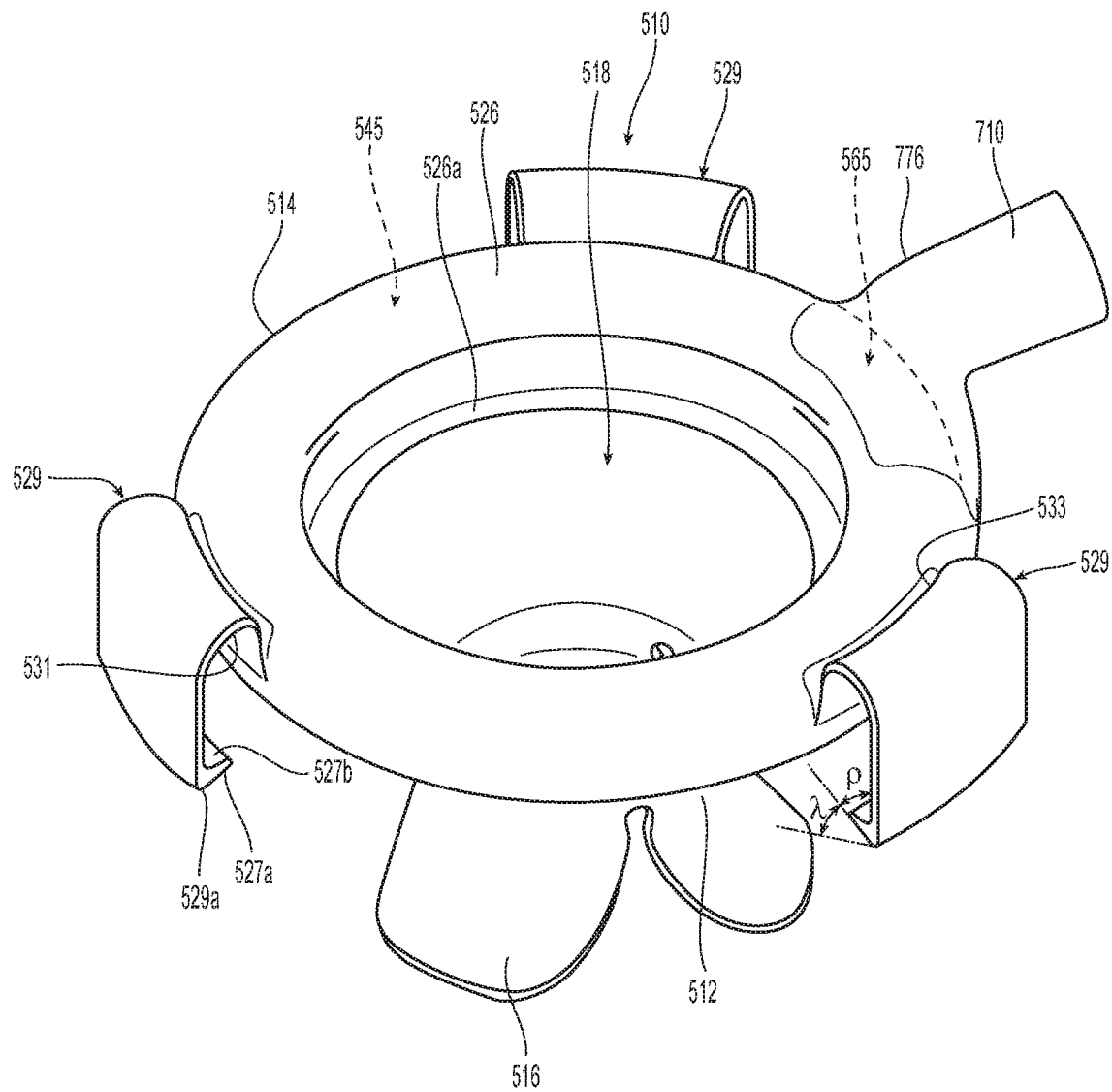
FIG. 3A is a top perspective view of another embodiment of a tissue guard for use with the access device.

Turning to FIGS. 1A and 1B, an exemplary system 100 provided in accordance with the present disclosure includes a tissue guard 110 and an access device 150. Tissue guard 110 is monolithically formed as a single piece of material, e.g., a biocompatible plastic such as, for example, polyethylene, polycarbonate, etc., from any suitable method, e.g., injection molding. The material, thickness, and configuration of tissue guard 110 are such that tissue guard 110 defines sufficient stiffness to maintain its shape when positioned within an opening in tissue "T" and/or when engaged within access device 150. However, the material, thickness, and configuration of tissue guard 110 also provide sufficient resilient flexibility to permit manipulation of tissue guard 110 from an at-rest position for insertion into an opening in tissue "T" and/or for engagement within access device 150, with tissue guard 110 returning to or towards the at-rest position after insertion and/or engagement as explained in more detail below. Further, the material, thickness, and configuration of tissue guard 110 is selected such that tissue guard 110 is configured to withstand cutting and puncturing by surgical knives, scalpels, pencils, and the like, thereby protecting surrounding tissue "T" and/or access device 150 from being cut or punctured. Tissue guard 110 may additionally or alternatively be configured to inhibit transfer of thermal and/or electrical energy therethrough to protect surrounding tissue "T" and/or access device 150 from thermal and/or electrical energy.

Continuing with reference to FIGS. 1A and 1B, tissue guard 110 includes a body 112 defining an open proximal end 114, an open distal end 116, and a lumen 118 extending therethrough between open proximal and distal ends 114, 116, respectively. Lumen 118 defines a longitudinal axis 120 and is configured to receive one or more surgical instruments (not shown) therethrough. In embodiments, body 112 defines a funnel-shaped configuration wherein a diameter of body 112 at open proximal end 114 thereof is greater than a diameter of body 112 at open distal end 116 thereof. Additionally or alternatively, the exterior surface 122 of body 112 may define a generally concave configuration while the interior surface 124 of body 112, which defines lumen 118, may define a generally convex configuration.

Access device 150 may be configured as a tissue retractor, an access port, or other suitable access device configured for positioning within an opening in tissue "T," e.g., a surgical incision or a naturally-occurring orifice, to provide access therethrough into an internal surgical site. Access device 150 includes a proximal rim 152 configured for positioning on an external side of the opening in tissue "T," a distal rim 154 configured for positioning on an internal side of the opening in tissue "T," and a body 156 extending between proximal and distal rims 152, 154, respectively. Body 156 is configured to extend through the opening in tissue "T" and defines a passageway 158 extending longitudinally therethrough to permit access to an internal surgical site through the opening in tissue "T." Passageway 158 defines a longitudinal axis 160. At least a portion of body 156 of access device 150 may be flexible to facilitate insertion and positioning of access device 150 within the opening in tissue "T." In embodiments, body 156 is formed from a flexible sleeve of material including one or more layers of material. Further, access device 150 may be selectively adjustable, e.g., by rolling proximal rim 154 distally about body 156, to retract tissue "T" and/or secure access device 150 within the opening in tissue "T." Access device 150 may further define an inwardly-extending overhang 162 between proximal rim 154 and body 156 and extending annularly about passageway 158.

As shown in FIG. 1B, in use, access device 150 is positioned within an opening in tissue "T" such that, as noted above, distal rim 154 is disposed on an internal surface of tissue "T" on the internal side of the opening in tissue "T," body 156 extends through the opening in tissue "T," and proximal rim 152 is disposed on an exterior surface of tissue "T" on the external side of the opening in tissue "T." As also noted above, access device 150 may be adjusted to conform access device 150 to a patient's anatomy, retracting tissue "T" and/or securing access device 150 within the opening in tissue "T." With access device 150 disposed within the opening in tissue "T," tissue guard 110, led by open distal end 116 thereof, is inserted into passageway 158.

Turning now to FIGS. 2A-2B, tissue guard 110 includes a lip 126 extending radially outwardly from open proximal end 114 of body 112 about the annular perimeter thereof. In this manner, lip 126 extends radially outwardly from lumen 118. Lip 126 may extend radially outwardly from body 112 at an oblique angle relative thereto. Lip 126 also includes an annular finger 129 extending from an outer peripheral surface thereof that is configured to anchor the tissue guard 110 within the access device 150. More particularly, annular finger 129 includes a flange 129a disposed at a distal end thereof that is configured to engage an underside of rim 152 of access device 150 to secure the tissue guard 110 therein. Finger 129 is configured to flex between an insertion position wherein the finger 129 is disposed in an abutting relationship with body 112 and a locking position wherein finger 129 flexes under a bias to engage flange 129a under rim 152 (FIG. 2B).

Flange 129a is angled to both facilitate insertion and to facilitate engagement. More particularly, an outer peripheral surface 127a of flange 129a is disposed at a first angle alpha (α) in the range from about 45 degrees to about 60 degrees to encourage the finger 129 and, hence, the tissue guard 110, to slip into lumen 118 and an inner peripheral surface 127b is disposed at second angle beta (β) in the range from about 60 degrees to about 80 degrees to facilitate engagement of flange 129a with the underside of rim 152 (FIGS. 2B and 2C).

In embodiments, finger 129 may be configured to "snap" into engagement with the underside of rim 152 and, in such embodiments, may produce an audible and/or tactile response that confirms the engagement of tissue guard 110 within access device 150.

With tissue guard 110 engaged within access device 150 as detailed above, surgical instrumentation may be inserted through lumen 118 of tissue guard 110 into the internal surgical site to, for example, extract a tissue specimen therefrom. Tissue guard 110, as noted above, protects tissue "T" as well as access device 150 during the insertion, manipulation, use and withdrawal of any such surgical instrumentation.

Figure 3B:
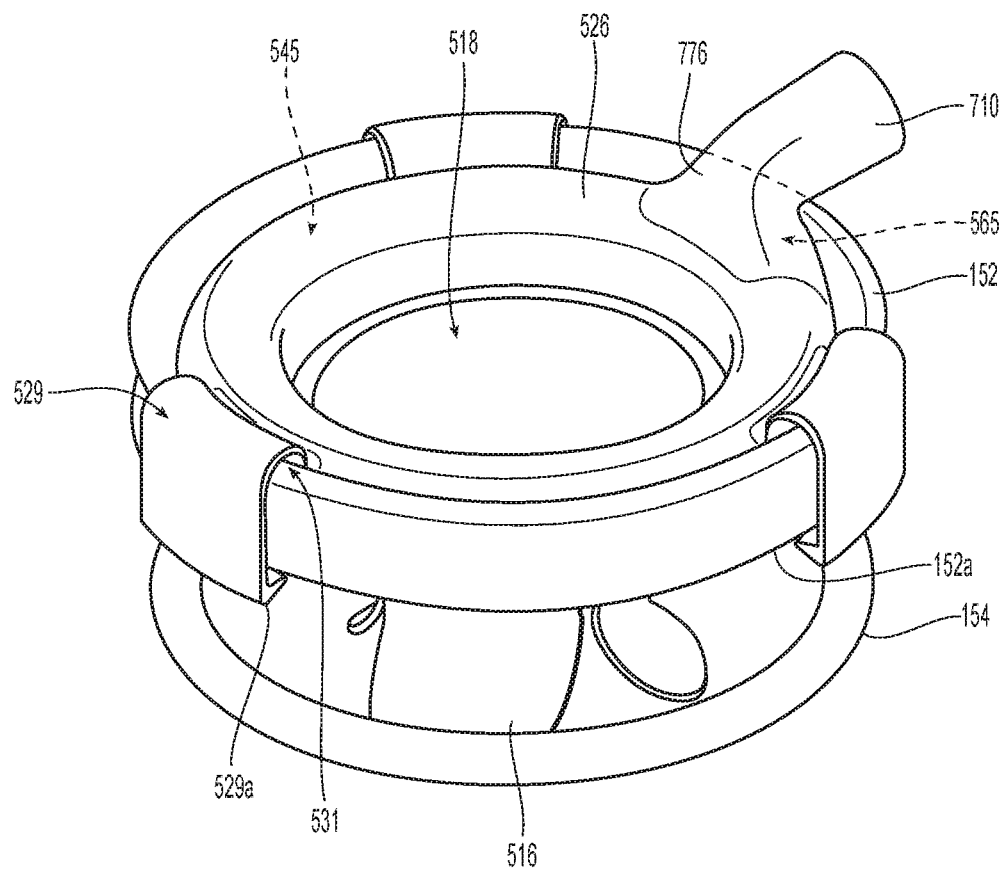
FIG. 3B is a top perspective view of the tissue guard of FIG. 3A engaged to a proximal rim of the access device.

Turning to FIGS. 3A-3B, another tissue guard 510 provided in accordance with the present disclosure is shown. With additional momentary reference to FIG. 2A, tissue guard 510 is similar to tissue guard 110 except as explicitly contradicted below and may be used in conjunction with access device 150 as part of a system similar to system 100. For purposes of brevity, only differences between tissue guard 510 and tissue guard 110 are detailed below, while similarities are summarily described or omitted.

Tissue guard 510 includes a body 512 defining an open proximal end 514, an open distal end 516, and a lumen 518 extending therebetween. A lip 526 extends radially outwardly from open proximal end 514 of body 512 and includes a plurality of fingers 529 extending from an outer peripheral surface thereof. The fingers 529 may be equidistantly-spaced about the lip 526 or may be spaced an any particular manner depending upon a particular purpose. In embodiments, a continuous finger (not shown) may be annularly spaced about the lip 526.

Each finger 529 includes an arcuate channel 531 defined along an inner peripheral surface thereof configured to at least partially encapsulate or mount atop rim 152 of the access device 150. More particularly, when the tissue guard 510 is first inserted into access device 150, channel 531 of each finger 529 aligns atop rim 152 of access device 150 and is poised for engagement atop rim 152 when the fingers 529 are secured. Each finger 529 also includes a flange 529a disposed at a distal end thereof that is configured to engage an underside of rim 152 to secure the tissue guard 510 in place. Finger 129 is configured to flex upon insertion of the tissue guard 510 into access device 150 by virtue of rim 152 forcing flange 529a and finger 529 outwardly as the tissue guard 510 is inserted. Upon full insertion of the tissue guard 510 into access device 150, the channel 531 of finger 529 encapsulates the rim 152 while the flange 529a snaps into place under rim 152 thereby locking the tissue guard 510 atop access device 150. The finger 529 is biased in the locked position. The flange 529a extends inwardly relative to the proximal ring 152 and operably engages the underside of the proximal ring 152 when biased.

Flange 529a may be angled to both facilitate insertion and to facilitate engagement. More particularly, an outer peripheral surface 527a of flange 529a may be disposed at a first angle lambda ($\lambda$) in the range from about 60 degrees to about 80 degrees to encourage the finger 529 and, hence, the tissue guard 510, to slip into lumen 118 and an inner peripheral surface 527b is disposed at second angle phi ($\varphi$) in the range from about 45 degrees to about 60 degrees to facilitate engagement of flange 529a with the underside of rim 152 (FIG. 3B). The shape of channel 531 may be dimensioned to conform to the shape of the outer peripheral surface of rim 152. Moreover, the height of the channel 531 may be dimensioned slightly larger than the thickness and depth of the rim 152 to facilitate engagement.

The distal end 516 of tissue guard 510 includes a plurality of scallop-like tabs 516a spaced-apart annularly thereabout. Scallop-like tabs 516a are configured engage an inner peripheral surface of body 112 of the access device 150 and are contoured or scalloped to generally mimic the shape thereof. The scallop-like tabs 516a are biased outwardly to maximize the opening at the distal end 516 of the tissue guard 510 and effectively secure the distal end 516 of the tissue guard 510 within access device 150 thereby facilitating surgical instrument access to the body cavity.

As mentioned above, lips 126, 526 define an annular channel therein configured to direct surgical exhaust therethrough to their respective ports 165, 565 defined in an outer peripheral surface of lips 126, 526. Lips 126, 526 include distal ends 126a, 526a that each extend inwardly therefrom towards lumens 118, 518 to form annular channels 145, 545 configured to direct surgical exhaust gas to ports 165, 565, respectively. One or more slits or passageways 113 (FIG. 12) may be defined within the inner peripheral surface of distal ends 126a, 526a that allow surgical gases passage into annular channels 145, 545, respectively. As explained in more detail below, each port 165, 565 is configured to connect to an exhaust connection 776 of a fluid management or smoke evacuation system 700 (FIG. 12). In other words, lips 126, 526 are each configured as generally hollow sleeves disposed proximate the inner peripheral surface of respective proximal ends 114, 514 of tissue guards 110, 510 and are configured to direct evacuation fluids and smoke to the exhaust connection 776 and to the fluid management or smoke evacuation system 700.

Figure 4A:
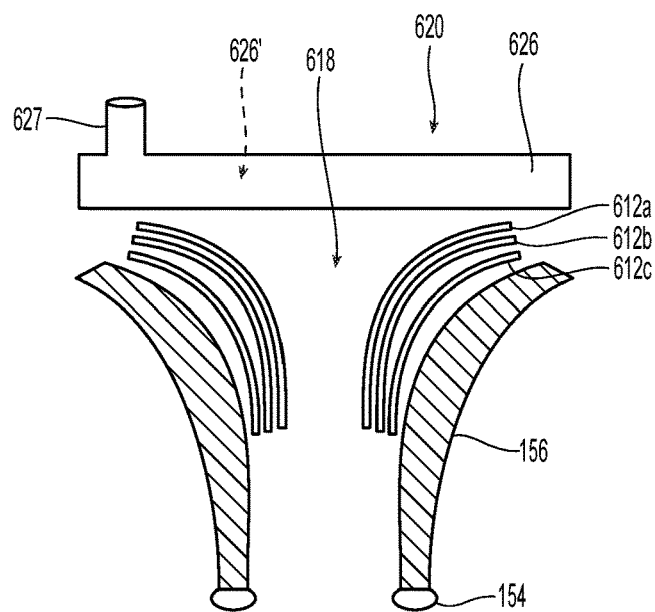
FIGS. 4A-4B is a system provided in accordance with the present disclosure including an access device, a series of tissue guards of varying lengths and a smoke evacuation ring.
Figure 4B:
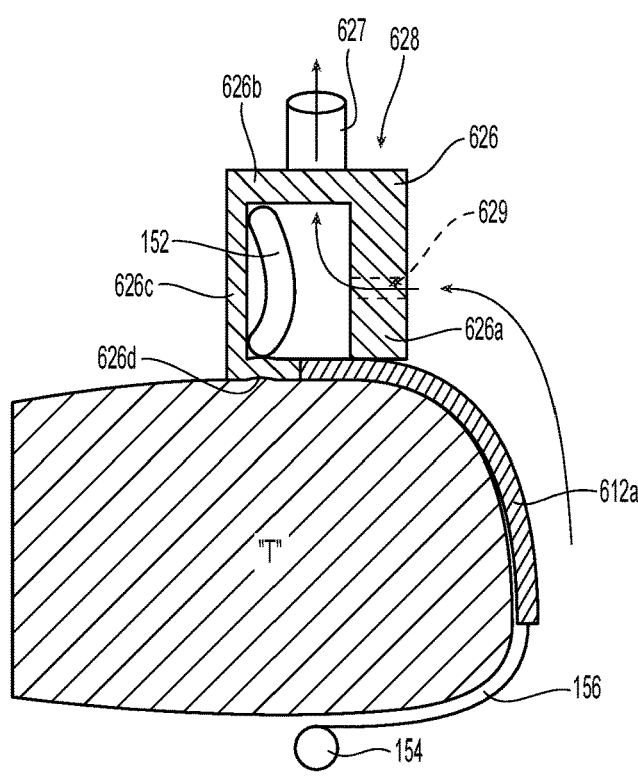

Turning to FIGS. 4A-4B, one embodiment of a smoke evacuation member is shown and is generally designated as reference numeral 620. Smoke evacuation member 620 includes an evacuation ring 626 that defines an annular channel 626' therein configured to convey smoke, odors and miscellaneous gases from the operating cavity to a smoke evacuation system 700 (FIG. 12). More particularly, evacuation ring 626 is generally annular in shape and includes a connection port 627 that operably couples to tubing 710 of the smoke evacuation system 700. Evacuation ring 626 is configured to operably couple to the proximal rim 152 of access device 150 (FIG. 4B) via one or more mechanically interfacing surfaces. More particularly, evacuation ring 626 is generally U-shaped and includes an inner peripheral edge 626a and an outer peripheral edge 626c connected via upper flange 626b. Upper flange 626b includes connection port 627 disposed thereon. A lower flange 626d extends inwardly towards the operating cavity at varying locations along the edge 626c (See FIG. 4B) and is configured to operably engage an underside of rim 152 to secure the evacuation ring 626 atop the access device 150 (See FIG. 4B).

Evacuation ring 626 is also configured to engage a wound guard, e.g., wound guard 612a, to secure the wound guard 612a within the access device 150. More particularly, inner peripheral edge 626a of the evacuation ring 626 may be configured to mechanically secure the wound guard 612a within access device 150 upon engagement with rim 152 thereof. Wound guards 612a-612c of varying length may be inserted and sized within access device 150 and, once the properly-sized wound guard, e.g., wound guard 612a, is in place, thereafter secured therein via coupling of the evacuation ring 626 thereon. Wound guards 612a-612c may vary in length from about 2 cm to about 8 cm.

In use, once the access device 150 is positioned within the operating cavity, the surgeon can insert one or more wound guards 612a-612c therein to size the wound guard, e.g., 612a, within the cavity. When the desired wound guard 612a is in place, the evacuation ring 626 is then secured to the proximal rim 152 thereby securing the wound guard 612a in place within the cavity.

During use, the wound guard 612a may be easily exchanged for a longer or shorter wound guard, e.g. 612c, and the evacuation ring 626 remounted atop the rim 152 to secure the same. As the tissue specimen is being excised, smoke emanating from the operating site is removed via the smoke evacuation system 700. More particularly, smoke is sucked under negative pressure from the operating cavity and through an aperture 629 defined in the inner peripheral edge 626a of ring 626 and to connection port 627. From the connection port 627, the smoke is transported via tubing 710 to the smoke evacuation system 700 (FIG. 12).

Figure 5:
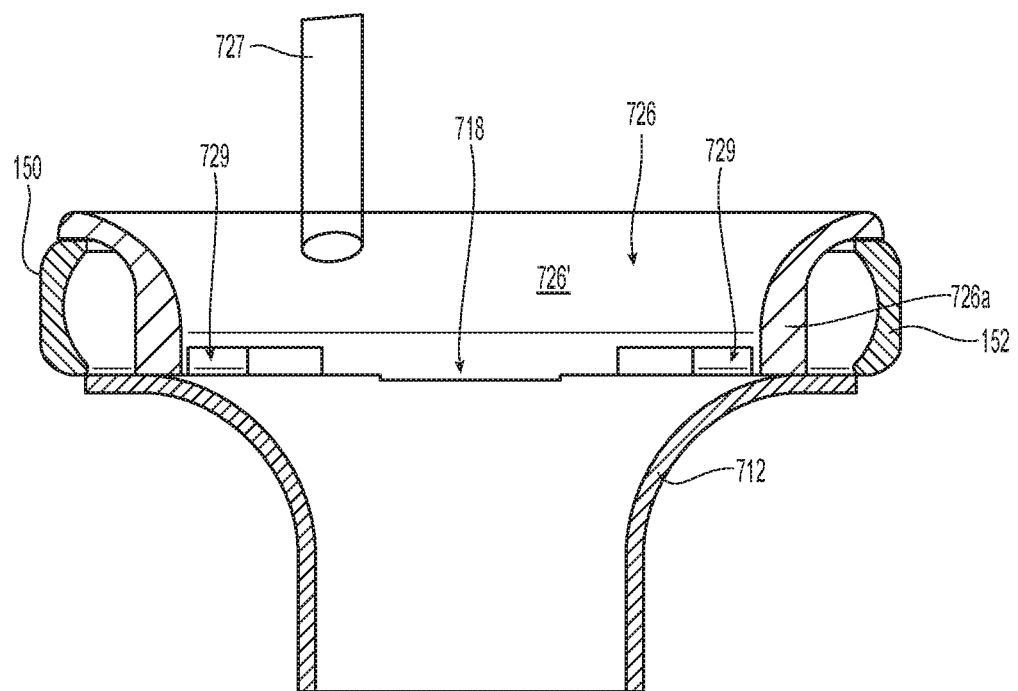
FIGS. 5-6D are various views of a smoke evacuation ring for use with one or more of the access devices and tissue guards of FIGS. 1A-4B.
Figure 6A:
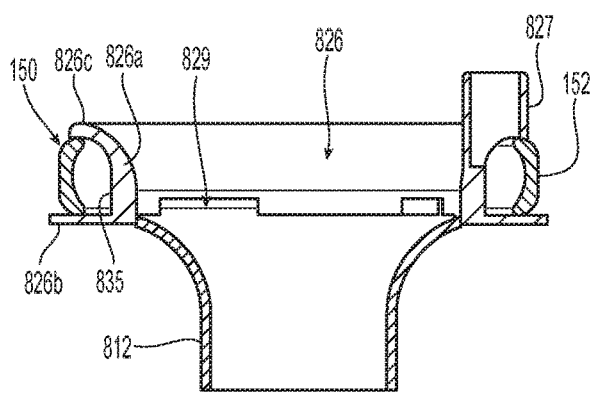
Figure 6B:
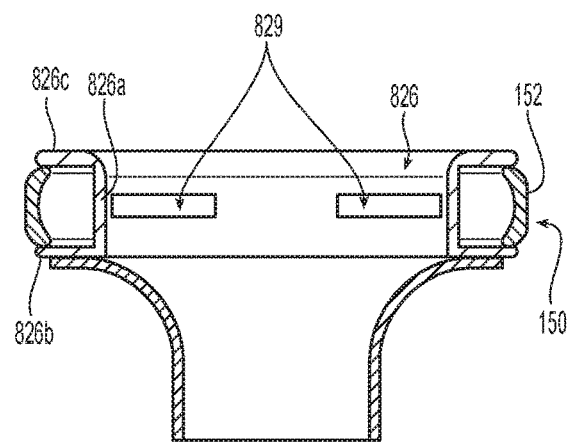
Figure 6C:
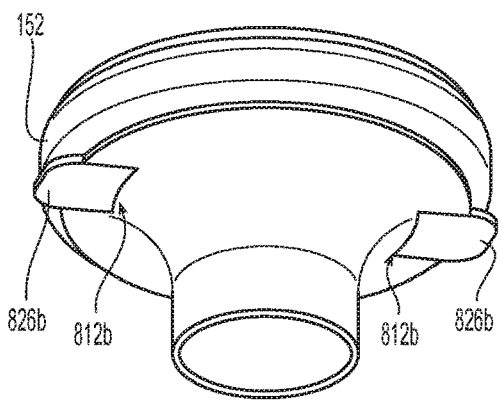
Figure 6D:
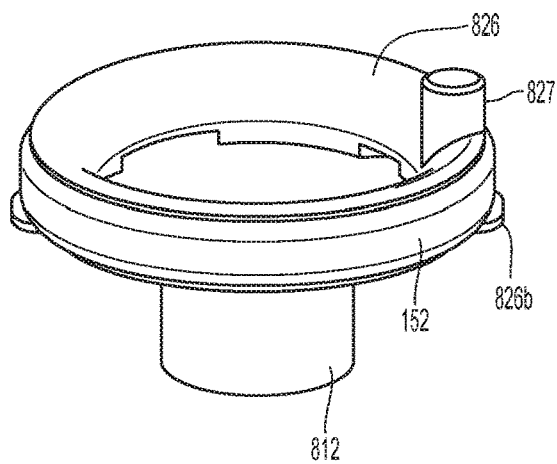

FIGS. 5-6D show additional embodiments of evacuation rings 726 and 826 for use with any of the systems and wound guards described herein. Evacuation ring 726 includes a generally circular shape having an inner peripheral surface 726' defining a series of channels 729 therein configured to communicate with the operating cavity (FIG. 5). Evacuation ring 726 is configured to snap atop the access device 150 and operably couple to the wound guard 712 to secure both the wound guard 712 and the access device 150 in place while at the same time allowing smoke to be safely and effectively evacuated through channels 729 to connection port 727 and, ultimately, to smoke evacuation system 700. The cross sectional profile of evacuation ring 726 is generally J-shaped to facilitate secure engagement both atop access device 150 and to wound guard 712. One or more mechanical interfaces (not shown) may be utilized to further secure the evacuation ring 726 to the access device 150 and/or wound guard 712, e.g., tabs, ridges, flanges, etc.

FIGS. 6A-6D show evacuation ring 826 for use with any of the systems and wound guards described herein. Evacuation ring 826 includes a generally circular shape having an inner peripheral surface 826a defining a series of channels 829 therein configured to communicate with the operating cavity. Evacuation ring 826 is configured to snap atop the access device 150 and operably couple to the wound guard 812 to secure both the wound guard 812 and the access device 150 in place while at the same time allowing smoke to be safely and effectively evacuated through channels 829 to connection port 827 and, ultimately, to smoke evacuation system 700.

The cross sectional profile of evacuation ring 826 is generally U-shaped to facilitate secure engagement both atop access device 150 and to wound guard 812. More particularly, the U-shaped cross section includes inner peripheral surface 826a having an upper flange 826c and a series of lower flanges 826b. Upper flange 826c is configured to operably couple atop (or otherwise mechanically engage) access device 150 and each of the series of lower flanges 826b is configured to operably couple (or otherwise mechanically engage) to wound guard 812. The lower flanges 826b may be arranged in opposing pairs about the evacuation ring 826. The evacuation ring 826 includes an outer peripheral surface 835 configured to complement an adjoining surface of the access device 150.

Wound guard 812 may include one or more apertures 812b defined thein configured to mechanically couple to a corresponding number of lower flanges 826b. An upper end of wound guard 812 may be resilient to facilitate engagement of the corresponding mechanical components. One or more mechanical interfaces (not shown) may be utilized to further secure the evacuation ring 826 to the access device 150, e.g., tabs, ridges, flanges, etc.

In use, the user inserts access device 150 into an operating cavity, inserts a wound guard 812 therein and then mounts the evacuation ring 826 atop rim 152 of the access device 150 while at the same time mechanically engaging flanges 826b within apertures 812b. This secures all of the components for use. The user simply reverse the process to uncouple the evacuation ring 826 from the wound guard 812 and access device 150.

Figure 7A:
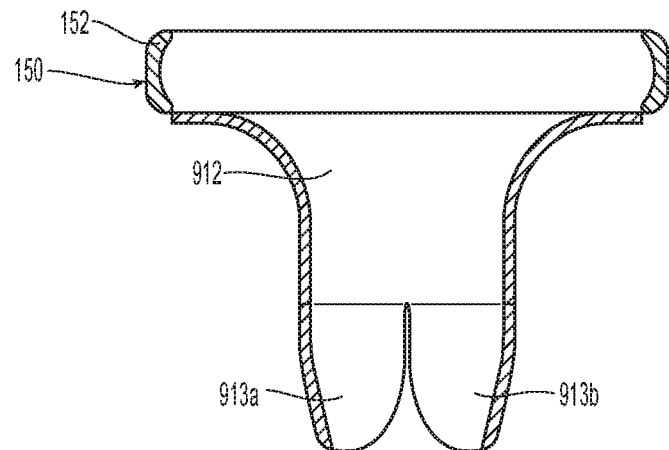
FIGS. 7A-7B are side, cross-sectional views of another embodiment of a smoke evacuation ring for use with one or more of the access devices and tissue guards of FIGS. 1A-6D.
Figure 7B:
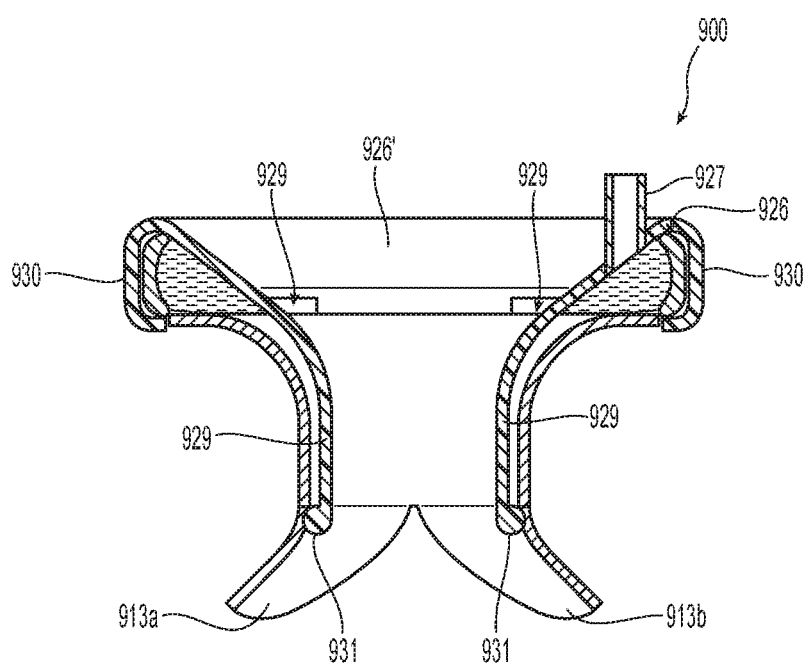

FIGS. 7A-7B show another embodiment of an evacuation ring 926 for use with any of the systems and wound guards described herein. Evacuation ring 926 includes a generally circular shape having an inner peripheral surface 926' defining a series of channels 929 therein configured to communicate with the operating cavity. Evacuation ring 926 also includes an elongated sleeve 929 that has a ring-like distal end 931. Evacuation ring 926 is configured to snap atop the access device 150 and operably couple inside the wound guard 912 to secure both the wound guard 912 and the access device 150 in place while at the same time allowing smoke to be safely and effectively evacuated through channels 929 to connection port 927 and, ultimately, to smoke evacuation system 700.

FIG. 7A shows the access device 150 and wound guard 912 prior to engagement with the evacuation ring 926. Wound guard 912 is bifurcated at a distal end thereof forming ends 913a and 913b. Prior to insertion of the evacuation ring 926, the natural bias of the material of the wound guard 912 maintains the ends 913a, 913b approximated thereby facilitating insertion into the operating cavity. Upon insertion of the evacuation ring 926, the ring-like distal end 931 of evacuation ring 926 forces the bifurcated distal ends 913a, 913b outwardly against the tissue of the operating cavity thereby locking the assembled components (e.g., access device 150, wound guard 912 and evacuation ring 926) in place for use. A locking flange 930 locks atop the access device 150 after insertion to secure the evacuation ring 926 about the rim 152 of the access device (FIG. 7B).

Figure 8A:
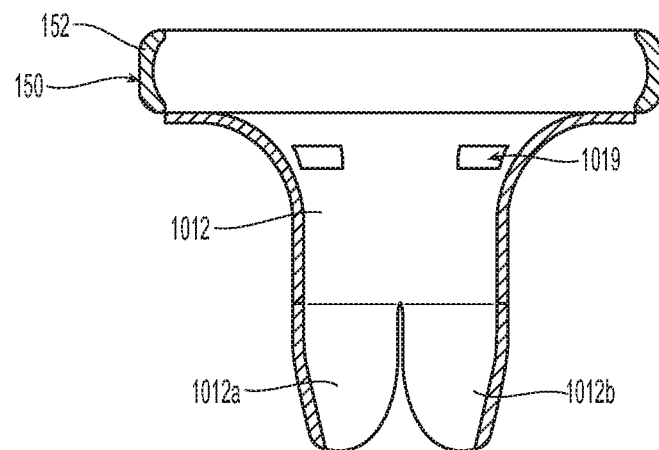
FIGS. 8A-8B are side, cross-sectional views of another embodiment of a smoke evacuation ring for use with one or more of the access devices and tissue guards of FIGS. 1A-6D.
Figure 8B:
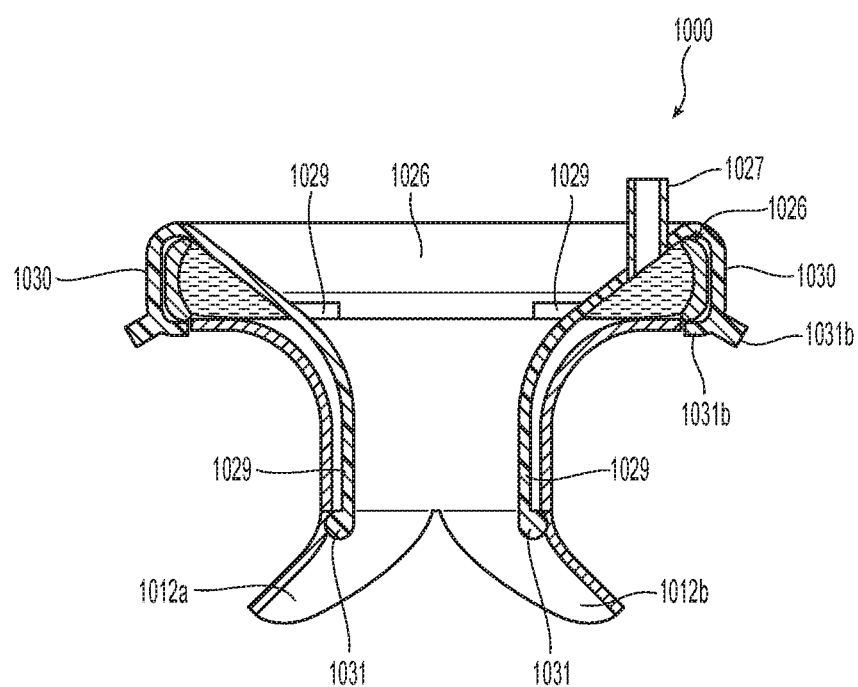

FIGS. 8A-8B show anther embodiment of an evacuation ring 1026 for use with any of the systems and wound guards described herein. Evacuation ring 1026 includes a generally circular shape having an inner peripheral surface 1026' defining a series of channels 1029 therein configured to communicate with the operating cavity. Evacuation ring 1026 also includes an elongated sleeve 1029 that includes a ring-like distal end 1031. Evacuation ring 1026 is configured to snap atop the access device 150 and operably couple inside the wound guard 1012 to secure both the wound guard 1012 and the access device 150 in place while at the same time allowing smoke to be safely and effectively evacuated through channels 1029 to connection port 1027 and, ultimately, to smoke evacuation system 700.

FIG. 8A shows the access device 150 and wound guard 1012 prior to engagement with the evacuation ring 1026. Wound guard 1012 is bifurcated at a distal end thereof forming ends 1013a and 1013b. Prior to insertion of the evacuation ring 1026, the natural bias of the material of the wound guard 1012 maintains the ends 1013a, 1013b approximated thereby facilitating insertion into the operating cavity. Upon insertion of the evacuation ring 1026, the ring-like distal end 1031 of evacuation ring 1026 forces the bifurcated distal ends 1013a, 1013b outwardly against the tissue of the operating cavity thereby locking the assembled components (e.g., access device 150, wound guard 1012 and evacuation ring 1026) in place for use. A locking flange 1030 locks atop the access device 150 after insertion to secure the evacuation ring 1026 about the rim 152 of the access device 150.

Locking flange 1030 is split at a distal end thereof forming locking end 1031a and release 1031b. Locking end 1031a is configured to curl under rim 152 to further secure the evacuation ring 1026 to the access device 150. Release 1031b projects opposite end 1031a and is configured to facilitate uncoupling the evacuation ring 1026 from the access device 150 when pulled. Wound guard 1012 includes one or more holes 1019 defined therein near a proximal end thereof that are configured to facilitate removal of the wound guard 1012 from the access device 150.

Figure 9A:
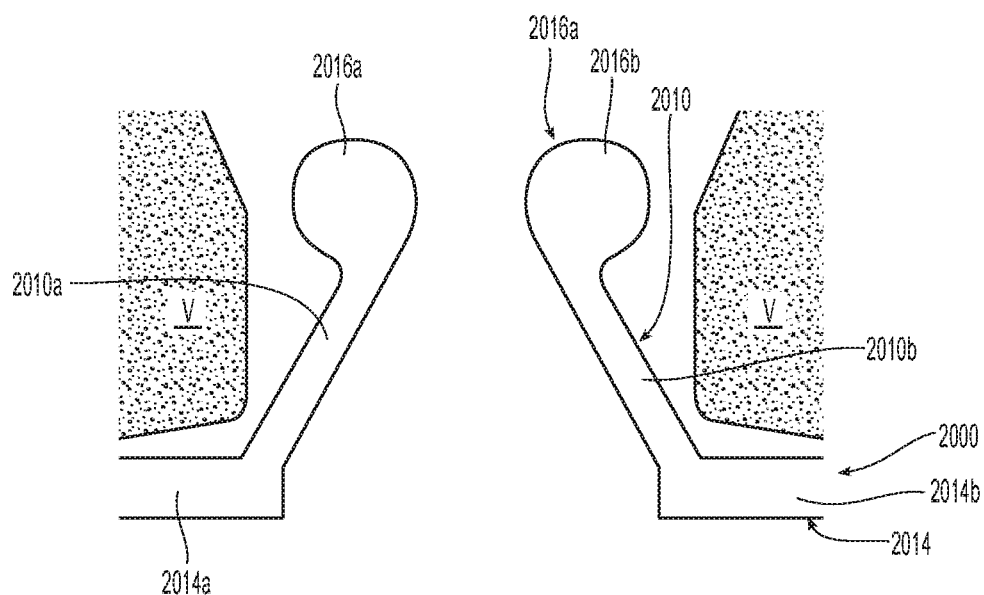
FIGS. 9A-9B are side, cross-sectional views of an access device and a tissue guard for use with vaginal surgeries.
Figure 9B:
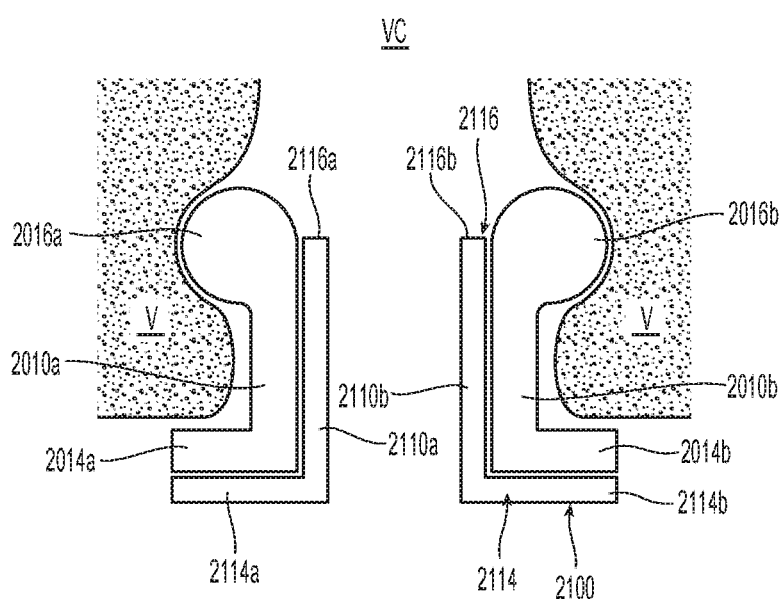

FIGS. 9A and 9B show an alternate embodiment of a wound guard 2100 for use with an access device 2000 for various types of vaginal surgeries, e.g. hysterectomies.

Wound guard 2100 operates in a similar fashion to evacuation rings 926, 1026 discussed above with respect to FIGS. 7A-8B. More particularly, access ring 2000 is placed inside the vaginal canal "VC" of a woman's vagina and the wound guard 2100 is inserted therein to secure the access device 2000 and wound guard 2100 in place for introduction of surgical instrumentation or surgical extraction of tissue.

Access device 2000 includes an elongated generally tubular sleeve 2010 (shown in cross section as sleeve sides 2010a, 2010b) having an annular rim 2014 disposed at a proximal end thereof and an anchor portion 2016 disposed at a distal end thereof. Annular rim 2014 is shown in cross section as rims 2014a and 2014b and anchor portion 2016 is shown in cross section as anchors 2016a and 2016b. Anchors 2016a, 2016b are made from a material that, prior to insertion, is naturally inwardly biased to reduce the annular diameter of the distal end of the access device 2000 to facilitate insertion.

Wound guard 2100 includes an elongated generally tubular sleeve 2110 (shown in cross section as sleeve sides 2110a, 2110b) having an annular rim 2114 disposed at a proximal end thereof and a biasing or anchoring ring 2116 disposed at a distal end thereof. Annular rim 2114 is shown in cross section as rims 2114a and 2114b and biasing portion 2016 is shown in cross section as biasing ends 2116a and 2116b. Likewise, in the cross sectional view, anchoring ring 2016 includes biasing ends 2016a, 2016b made from a material that, during insertion, is naturally outwardly biased to expand the annular diameter of the distal end of the access device 2000 to facilitate engagement of the access device 2000 to the vaginal walls.

In use, the access device 2000 is inserted into the vaginal canal "VC" with the annual rim 2014 remaining outside the vaginal opening. The biasing portion 2116 of the wound guard 2100 is squeezed to reduce the annular profile (e.g., distance between biasing ends 2116a, 2116b) to facilitate insertion of the wound guard 2100 into the access device 2000. Once inserted, the biasing portion is released forcing the anchor portion 2016 against the vaginal wall (i.e., the anchors 2016a, 2016b are wedged into the vaginal wall) thereby securing the access device 2000 and wound guard 2100 in place for use. After surgery, the wound guard 2100 is removed allowing the access device 2000 and anchors 2016a, 2016b to return to their natural inwardly-biased configuration facilitating removal from the vaginal canal "VC".

The cross sectional profile of the anchoring ring 2016 (or ends 2016a, 2016b) may be bulbous to facilitate engagement with tissue within the vaginal canal. Moreover, the proximal ring 2114 of the wound guard 2100 is configured to seat atop the proximal ring 2014 of the access device 2000. The anchoring ring 2016 of the access device 2000 may be split to include a series of anchoring portions or ends, e.g., 2016a, 2016b configured in a ring-like manner.

Figure 10A:
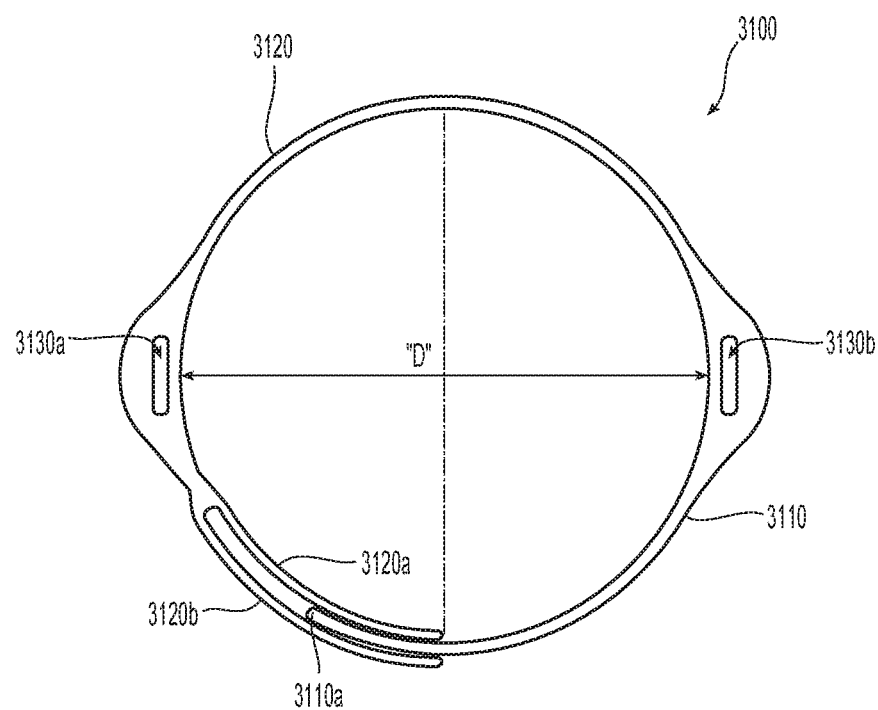
FIGS. 10A-10B are various views of an adjustable tissue or wound guard for use with one or more of the access devices of FIGS. 1A-6D.
Figure 10B:
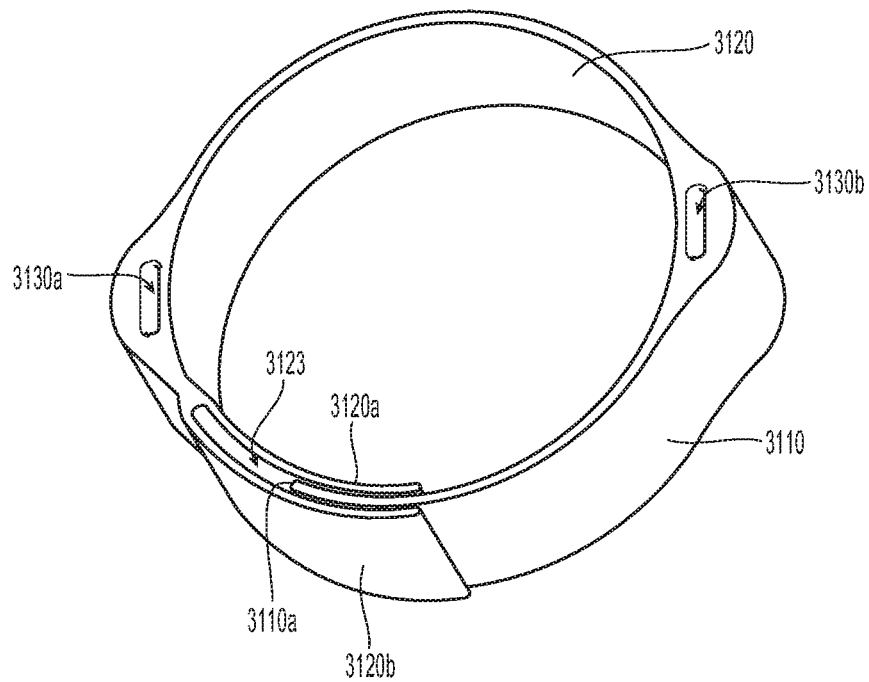
Figure 11:
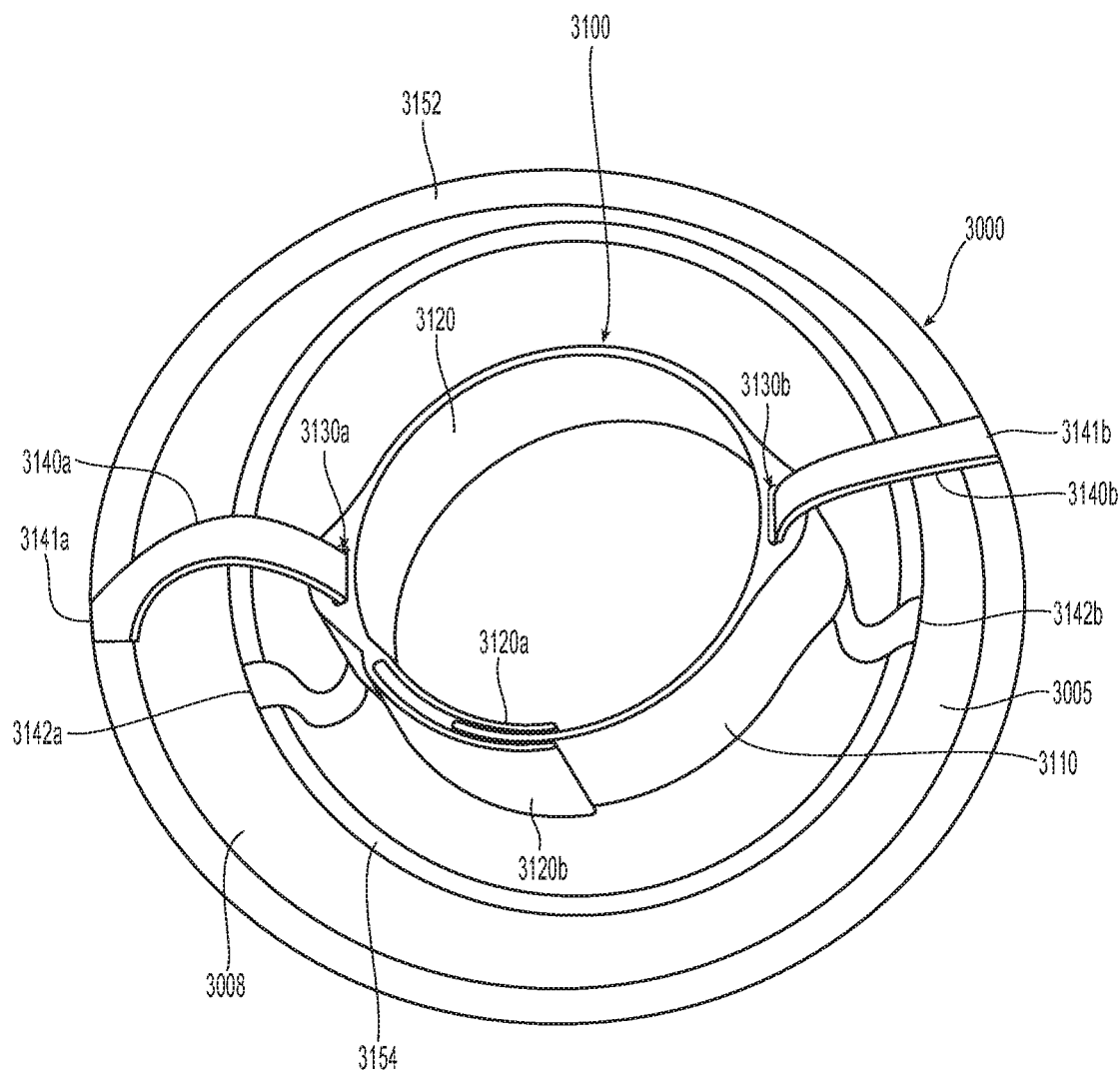
FIG. 11 is a top perspective view of the wound guard of FIGS. 10A and 10B shown attached to an access device.

FIGS. 10A-11 show an alternate embodiment of a wound guard 3100 for use with an access device 3000 for various types of surgeries. Access device 3000 includes upper and lower rims 3152, 3154, respectively, joined by an elongated sleeve 3005. Wound guard 3100 operates in a similar fashion and is made from similar materials as those described above and, as such, only the differences are described in detail. More particularly, wound guard 3100 includes a generally circular shape including two arcuate portions 3110 and 3120 that are configured to interleave with one another to allow a user to alter the diameter "D" of the wound guard 3100 for a particular purpose. Arcuate section 3110 includes a solid distal end 3110a and arcuate section 3120 includes two distal end portions 3120a, 3120b that define an elongated slot 3123 therebetween configured to receive distal end 3110a.

Both arcuate portion 3110 and 3120 also include strap slots 3130a and 3130b defined therein and configured to receive a respective strap 3140a, 3140b therethrough. More particularly, strap slot 3130a is configured to receive strap 3140a therethrough while strap 3140a is secured at end 3141a to upper rim 3152 and at end 3142a to lower rim 3154 of access device 3000. Strap slot 3130b is configured to receive strap 3140b therethrough while strap 3140b is secured at end 3141b to upper rim 3152 and at end 3142b to lower rim 3154 of access device 3000.

In use, the user inserts rim 3154 into an incision or vaginal canal allowing rim 3154 to expand and engage against the internal tissue of the wound or canal. As described above, rim 3152 is then rolled toward the incision (or canal) to expand the incision and further secure the access device 3000 in place within the wound or natural orifice. As rim 3152 is being rolled, the straps 3140a, 3140b are pulled causing the interleaved arcuate portions 3110, 3120 to correspondingly move to effectively size the diameter "D" of the wound guard 3100 within the access device 3000. Rim 3152 is then secured within access device 3000 with the wound guard 3100 properly sized therein.

Turning to FIG. 12, smoke evacuation system 700 is provided in accordance with the present disclosure and is shown generally including tissue guard 110, tubing 710, 720, a collection reservoir 730, and a smoke evacuation (or vacuum) source 740. The various tissue guards disclosed herein are all designed to work with system 700. Tissue guard 110 and tubing 710 are detailed above and are coupled to one another, e.g., via engagement of one end of tubing 710 about exhaust connection 776 of tissue guard 710. The other end of tubing 710 extends into collection reservoir 730 in sealing relation therewith.

Collection reservoir 730 includes a base 732 and a lid 734 sealed about base 732. Lid 734 defines first and second ports 736, 738 configured to receive ends of tubing 710, 720, respectively, in sealing relation therewith. These ends of tubing 710, 720 extend into the interior volume 733 of base 732 and are spaced-apart from one another as well as the bottom of base 732. Tubing 720 extends from collection reservoir 730 to smoke evacuation source 740 wherein the other end of tubing 720 is coupled to smoke evacuation source 740. In this manner, upon activation of smoke evacuation source 740, suction is established through lip 126 of tissue guard 110, tubing 710, collection reservoir 730, tubing 720, to smoke evacuation source 740. During use, this suction, in addition to evacuating smoke from tissue guard 110, may also suction liquids, tissue, and/or debris through tubing 710. However, as a result of the ends of tubing 710, 720 being spaced-apart from one another within collection reservoir 730 and spaced-apart from the bottom of base 732 of collection reservoir 730, the liquids, tissue, and/or debris are suctioned into collection reservoir 730 and deposited therein, while only the smoke and other gaseous fluids are further suctioned from collection reservoir 730 through tubing 720 to smoke evacuation source 740. As such, smoke evacuation source 740 is protected by inhibiting suctioning of liquids, tissue, and/or debris into smoke evacuation source 740.

From the foregoing and with reference to the various drawings, those skilled in the art will appreciate that certain modifications can be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical system for accessing an operating cavity, comprising:
    an access device configured for insertion within an operating cavity, the access device including an elongated sleeve having proximal and distal rims disposed on opposing ends of the elongated sleeve, the distal rim configured for insertion within an operating cavity and the proximal rim configured to seat against tissue outside the operating cavity; and
    a wound guard configured for insertion within the access device, the wound guard including a pair of interleaved arcuate portions defining a diameter of the wound guard and each having a strap slot configured to receive a respective strap, each strap including a proximal end fixedly attached to the proximal rim of the access device and a distal end fixedly attached to the distal rim of the access device, wherein movement of the proximal rim relative to the distal rim applies tension on the respective straps to cause the pair of interleaved arcuate portions to move relative to one another to adjust the diameter of the wound guard relative to the access device.

2. The surgical system for accessing an operating cavity according to claim 1, wherein adjustment of the proximal rim of the access device to secure the access device within the operating cavity simultaneously adjusts the pair of interleaved arcuate portions to size the wound guard within the access device.

3. The surgical system for accessing an operating cavity according to claim 1, wherein the wound guard is configured to inhibit transfer of at least one of thermal energy or electrical energy.

4. The surgical system for accessing an operating cavity according to claim 1, wherein the pair of interleaved arcuate portions includes a first arcuate portion having a solid distal end and a second arcuate portion having a split distal end defining an elongated slot configured to receive the solid distal end of the first arcuate portion.

5. The surgical system for accessing an operating cavity according to claim 4, wherein the pair of interleaved arcuate portions are flexibly resilient to permit manipulation of the wound guard between an at-rest position for insertion into an operating cavity and an engagement position for engagement within the access device.

6. The surgical system for accessing an operating cavity according to claim 1, wherein the wound guard is monolithically formed as a single piece of a biocompatible material.

7. The surgical system for accessing an operating cavity according to claim 6, wherein the biocompatible material is one of polyethylene or polycarbonate.

8. A method for accessing a surgical cavity, comprising:
    inserting a distal rim of an access device within an operating cavity such that a proximal rim, disposed at an opposing end of the access device from the distal rim, seats against tissue disposed on an outer surface of the operating cavity;
    inserting a wound guard having a pair of interleaved arcuate portions defining a diameter within the access device, each arcuate portion including a pair of strap slots configured to receive a respective strap fixedly attached at one end to the proximal rim of the access device and at an opposing end to the distal rim of the access device; and
    moving the proximal rim relative to the distal rim, thereby tensioning the pair of straps to cause the pair of interleaved arcuate portions to move relative to one another to adjust the diameter of the wound guard within the access device to abut the wound guard against tissue within the operating cavity.

9. The method for accessing a surgical cavity according to claim 8, wherein tensioning the pair of straps simultaneously secures the access device within the operating cavity.

10. The method for accessing a surgical cavity according to claim 8, wherein the wound guard is monolithically formed as a single piece of a biocompatible material.

11. The method for accessing a surgical cavity according to claim 8, wherein the wound guard is configured to inhibit transfer of at least one of thermal energy or electrical energy.

12. The method for accessing a surgical cavity according to claim 8, wherein the method includes flexing the pair of interleaved arcuate portions to permit manipulation of the wound guard for insertion within the access device.

13. The method for accessing a surgical cavity according to claim 12, wherein the biocompatible material is one of polyethylene or polycarbonate.

* * * * *